United States Patent [19]

Harris et al.

[11] 4,289,748
[45] Sep. 15, 1981

[54] ULTRASENSITIVE ENZYMATIC RADIOIMMUNOASSAY METHOD

[75] Inventors: Curtis C. Harris, Bethesda; Robert Yolken, Laurel; Ih-Chang Hsu, Rockville, all of Md.

[73] Assignee: United States of America, Washington, D.C.

[21] Appl. No.: 44,260

[22] Filed: May 31, 1979

[51] Int. Cl.³ .................. G01N 33/48; G01T 1/00; G01N 33/54
[52] U.S. Cl. .................. 424/1; 23/230 B; 424/12; 435/7
[58] Field of Search .................. 424/1, 12; 23/230 B; 435/7

[56] References Cited

U.S. PATENT DOCUMENTS

| Re. 29,169 | 4/1977 | Schuurs et al. | 435/7 |
|---|---|---|---|
| 3,565,987 | 2/1971 | Schuurs | 424/12 |
| 3,646,346 | 2/1972 | Catt | 250/83 |
| 3,654,090 | 4/1972 | Schuurs et al. | 435/7 |
| 3,720,760 | 3/1973 | Bennich et al. | 424/1 |
| 3,790,663 | 2/1974 | Garrison et al. | 424/12 |
| 3,791,932 | 2/1974 | Schuurs et al. | 435/7 |
| 3,839,153 | 10/1974 | Schuurs et al. | 435/7 |
| 3,850,752 | 11/1974 | Schuurs et al. | 435/7 |
| 3,879,262 | 4/1975 | Schuurs et al. | 435/7 |
| 4,016,043 | 4/1977 | Schuurs et al. | 435/7 |
| 4,048,298 | 9/1977 | Niswender | 424/1.5 |
| 4,097,338 | 6/1978 | Konttinea | 195/103.5 R |
| 4,152,411 | 5/1979 | Schall | 424/1 |
| 4,169,012 | 9/1979 | Dawson et al. | 435/7 |
| 4,193,982 | 3/1980 | Avrameas et al. | 435/174 |
| 4,200,508 | 4/1980 | Hirai | 204/180 |

FOREIGN PATENT DOCUMENTS

| 2530621 | 1/1976 | Fed. Rep. of Germany | 23/230 B |
|---|---|---|---|
| 2530957 | 12/1976 | Fed. Rep. of Germany | 424/1 |
| 48-49919 | of 0000 | Japan | 424/1 |
| 53-45288 | of 0000 | Japan | 23/230 B |
| 53-47517 | of 0000 | Japan | 435/7 |
| 7501215 | 8/1976 | Netherlands | 424/1 |
| 1192784 | 5/1970 | United Kingdom | 424/12 |
| 1247896 | 9/1971 | United Kingdom | 424/12 |
| 1248764 | 10/1971 | United Kingdom | 424/1 |
| 1248765 | 10/1971 | United Kingdom | 424/1 |
| 1304045 | 1/1973 | United Kingdom | 424/12 |
| 1314263 | 4/1973 | United Kingdom | 424/12 |
| 1317787 | 5/1973 | United Kingdom | 424/1 |
| 1356346 | 6/1974 | United Kingdom | 424/12 |
| 1378103 | 12/1974 | United Kingdom | 424/1 |
| 1414479 | 11/1975 | United Kingdom | 422/61 |
| 1414480 | 11/1978 | United Kingdom | 424/1 |
| 1497327 | 1/1978 | United Kingdom | 424/1 |

OTHER PUBLICATIONS

Engvall et al., J. Immunol., vol. 109, (1972), pp. 129-135.
Yolken et al., J. Clin. Microbiol., vol. 6, (1977), pp. 439-444.
Yolken et al., The Lancet, Aug. 6, 1977, pp. 263-267.
Yolken et al., Science, vol. 201, Jul. 21, 1978, pp. 259-262.
Greenberg et al., Inf. Immunity, vol. 17, Sep. 1977, pp. 541-545.
Schuurs et al., Z. Anal. Chem. Band., 279, (1976), p. 142.

Primary Examiner—Deborah L. Kyle
Assistant Examiner—Christine M. Nucker
Attorney, Agent, or Firm—Holman & Stern

[57] ABSTRACT

A method of quantitatively measuring antigen or antibody concentration by selectively coupling an antigen to a solid substrate, coupling an enzyme-conjugated antibody to the antigen and reacting a radioindicator with the enzyme-conjugate producing a radiolabelled product. The product is scintillation counted to yield the measurement. Direct or indirect coupling of the antigen to the substrate can be used. Direct or indirect coupling of the enzyme-conjugate can be used. The preferred radioindicator is adenosine-5'-monophosphate used with alkaline phosphatase. Others are presented.

20 Claims, 6 Drawing Figures

ULTRASENSITIVE ENZYMATIC RADIOIMMUNOASSAY METHOD

BACKGROUND OF THE INVENTION

The present invention relates to a method for quantitatively measuring an immunosystem reactant, specifically, an antigen or an antibody. More particularly, the present method is an ultrasensitive enzymatic radioimmunoassay method.

Various methods are known to quantitatively and qualitatively measure antigens and antibodies in complex mixtures and solutions such as body fluids from humans and other animals, and laboratory and environmental specimens. Antigens can include viruses, bacteria, parasites, hormone toxins, tumor markers, drugs, and the like. The measurements are useful for diagnostic, prognostic, epidemiological, and experimental purposes.

Solid-phase radioimmunoassay methods are known in the art. These assays have been especially useful for the detection of immunosystem reactants. In general, a radioimmunoassay comprises preparing a solid substrate, selectively coupling the immunosystem reactant to the substrate, and then coupling a radiolabelled antibody to the reactant. After washing away any uncoupled radiolabelled antibodies, the radioactivity of the coupled antibody is measured by radioactive counting methods, for example, gamma or scintillation counting. The counting yields a quantitative determination of the amount of immunosystem reactant bound to the solid substrate. Generally, the radiolabelled antibody is labelled with the radioisotope iodine$^{131}$ or iodine$^{125}$. Generally, radioimmunoassay (RIA) can measure down to $10^{-12}$ grams per milliliter of material being tested for.

RIA is subject to certain disadvantages. Since the actual antibody is radiolabelled, either the solution must be made up shortly before use or a large stock of various different solutions must be held in inventory. The short half-life of the isotopes utilized limits the shelf life of the reagents. It is known that iodine$^{131}$ and iodine$^{125}$ subject the users of RIA to a definite biohazard. Radioiodine is expensive. The radioactive labelling of any compound can cause a number of secondary changes in the compound that may affect its properties and its behaviour in an assay system. If the radionuclide used for the labelling is an isotope of an element already present in the native unlabelled molecule and if the labelling involves only the simple substitution of the radioactive isotope for the non-radioactive one, then the labelled compound might be assumed to have the identical chemical and immunologic properties as the unlabelled. However, this ideal situation is seldom realized.

The decay of the radioactive label releases a certain amount of energy that is much higher than the energy involved in the chemical bonds that maintain the molecular structure of the compound. Therefore, decay can easily break adjacent bonds and cause disintegration of the molecular structure. Additionally, when a new element is formed from the decay of the radiolabel, the structure of the original molecule can be altered to the extent that the molecule will disintegrate or no longer serve the purpose for which it is intended. If the labelled molecule contains only a single radioactive atom, the problem that the molecule remaining after a decay event will not be the site of any further decay events leaves that molecule unlabelled and hence unmeasurable. Thus, the useful period of a material is shorter than could be expected from the simple half-life of the radioisotope alone.

If it is necessary to perform labelling by introducing a radioactive isotope that is not a normal component of the unlabelled material, not only will radiation change the material, but the chemical composition of the radiolabelled material may be different from that of unlabelled material. It has been shown that iodination as such can influence the potency of biologically active material. Additionally, the chemical properties of the radiolabelled material may be altered not only by the presence of a radioactive element that is not a normal constituent of the native molecule but also by the procedures used to introduce the radiolabel into the compound. Thus, RIA is subject to a number of disadvantages.

Enzyme immunoassays (also known as EIA and as enzyme-linked immunosorbent assays or ELISA) have been developed in an attempt to overcome the problems associated with RIA. ELISA is similar in design to solid-phase RIA described above except that an enzyme is utilized as the antibody marker instead of the radioisotope. This enzyme-antibody conjugate is bound to the solid-phase substrate by a series of antibody-antigen reactions and is utilized to convert an indicator material to produce a visible color. This color is measured spectrophotometrically. The fact that a single molecule of enzyme is capable of reacting with a large number of indicator molecules provides for amplification of the results and thus provides a high degree of sensitivity. An example of a suitable enzyme is alkaline phosphatase which can be used with p-nitrophenylphosphate which when hydrolyzed liberates a yellow p-nitrophenolate which is measured in a spectrophotometer at 400 nanometers. ELISA has the advantage over RIA in that the reagents that are used, namely the enzyme-conjugated antibody has a longer self life, is not subject to radiodecay effects and does not pose much of a biohazard to laboratory workers.

In practice, however, the sensitivity of ELISA has not significantly exceeded that of RIA. Specifically, ELISA can give results down to $10^{-13}$ grams per milliliter of material being tested.

OBJECTS AND SUMMARY OF THE INVENTION

It is an object of the present invention to provide an assay method for an immunosystem reactant (antigen or antibody) which is more sensitive than either ELISA or RIA.

It is a further object of the present invention to provide an immunoassay method which presents a lesser biohazard to laboratory workers and is less expensive than RIA.

It is a yet further object of the present invention to provide an immunoassay system which is simple to use.

Another object of the present invention is to provide a radioimmunoassay method which has a lower probability of radiodegradation of radiolabels, thus giving more accurate results and a longer shelf life.

Yet another object of the present invention is to provide a method usable for a wide variety of tests to quantitatively and qualitatively measure antigens, e.g., viruses, bacteria, parasites, hormones, toxins, tumor markers, drugs, etc., and antibodies in complex mixtures and solutions, such as body fluids and environmental specimens for diagnostic, prognostic, epidemiological and experimental purposes.

The present invention is a method of quantitatively measuring the concentration of an immunosystem reactant which comprises: preparing a solid substrate; selectively coupling the immunosystem reactant to the solid substrate; coupling an enzyme-conjugated antibody to the reactant; reacting a radiolabelled indicator with the enzyme-conjugated antibody thereby producing a radiolabelled product; separating the radiolabelled products and the unreacted indicator; and measuring the extent of reaction by radioactive counting the radiolabelled product, the counting yielding a quantitative measurement of the reactant concentration. The inventive method can be used when the immunosystem reactant is an antigen or an antibody.

When the immunosystem reactant is an antigen, it can be directly linked to the substrate by adsorption, electrostatic bonding, covalent bonding, or the like. Preferably, the antigen is coupled to the substrate through the use of an antigen-reactive antibody. The antigen-reactive antibody is adhered to the substrate using adsorption, electrostatic bonding, covalent bonding, and the like. The antigen-reactive antibody is specific for the particular antigen being measured. The antigen being measured reacts with the adhered antibody thus coupling the antigen to the substrate.

The coupling of the enzyme-conjugated antibody to the antigen can be either direct or indirect. When the coupling is direct, the enzyme-conjugated antibody is selected to be specific for the antigen being measured and the coupling is accomplished by directly reacting the enzyme-conjugated antibody with the coupled antigen. When the coupling is indirect, an unconjugated antigen specific antibody is reacted to the coupled antigen. The unconjugated antibody is from a different animal source than the antibody which is preferably adhered to the substrate. The enzyme-conjugated antibody is reacted with the unconjugated antibody linked to the antigen. The enzyme-conjugated antibody in this case is selected from the group of antibodies which are directed against the immunoglobulin subclass of the animal source of the unconjugated antibody. Thus, the coupled antigen and unconjugated antibody act as a combined antigen to the enzyme-conjugated antibody. The subclasses of immumoglobulin that could be used are IgG, IgM, IgA, IgE, and IgD. The preferred method selects the enzyme-conjugated antibody from the group directed against IgG subclass of the animal source of the unconjugated antibody. Thus, since the enzyme—conjugated antibody is directed against the broad class structure of the unconjugated antibody which is specific to the particular antigen being measured, a smaller number of previously prepared reagent solutions are needed in inventory. For example, specific animal antibodies can be prepared for specific antigens such as guinea pig anti-cholera toxin, burro anti-cholera toxin, goat anti-rotavirus etc. These antibodies are specific for specific antigens. Similarly, more general anti-immunoglobulin subclass antibodies can be prepared. For example, these could include sheep anti-rabbit globulin, goat anti-guinea pig IgG, and the like. These serums/antibodies are well known in the art.

As stated above, with regard to the direct linking of the enzyme-conjugated antibody to the antigen, in the indirect method, the antigen can be bound to the substrate by being reacted to an antigen-reactive antibody, specific to the antigen which is adhered to the substrate.

The adherence of the antigen-reactive coupling antibody to the substrate can be by adsorption, electrostatic bonding, covalent bonding or the like. The particular methods of adhering the antigen-reactive antibody to the substrate are known in the art.

Additionally, the present inventive method can also be utilized when the immunosystem reactant being measured is a single specific antigen-reactive antibody of a particular animal source. For this particular utilization, an antigen is coupled to the substrate, either by direct coupling or via an antibody adhering to the substrate. The particular antigen is specific to the particular antibody being measured. A solution or serum containing the antibody to be measured is reacted with the coupled antigen thereby adhering the antibody being measured to the coupled antigen. An enzyme-conjugated antibody is reacted with the adhered antibody being measured. The enzyme-conjugated antibody is selected from the group directed against the immunoglobulin subclass of the animal source of the antibody being measured. Thus, the enzyme-conjugated antibody is coupled to the adhered antibody being measured. This method is generally known in the art as a binding assay.

Many different radioindicator-enzyme systems would be readily apparent to any person having ordinary skill in the art. The requirements for these systems are that the radioindicator must be stable, the enzyme must be simple and easy to link to an antibody, the system must have high activity, and high purity. The products of reaction between the radioindicator and the enzyme should be easily separable using conventional techniques. A preferred enzyme-radioindicator system in the present invention is alkaline phosphatase-adenosine-5'-monophosphate. Upon reaction, adenosine-5'-monophosphate splits into adenosine and phosphate. Other suitable systems include alkaline phosphatase and p-nitrophenylphosphate, phosphatase and uricylphosphate, peroxidase and o-phenylenediamine, peroxidase and N, N, N', N'-tetramethylbenzydene, peroxidase and 3,3'-diaminobenzyldinetetrachloride, ribonuclease and RNA, beta-glucuronidase and o-aminophenyl-beta-z-glucuronide, and beta-glucuronidase and p-hitrophenyl-glucuronide. An example of a commonly used method of covalently linking the enzyme with the particular desired antibody is known in the art and described, for example, in *First International Symposium on Immuno-Enzymatic Techniques,* edited by G. Feldman (North Holland Publishing Company, Amsterdam) by Engvall, et al. (which is incorporated by reference herein).

The particular radiolabelling of the radioindicator would also be readily apparent to a person having ordinary skill in the art. In the case of the particular preferred radioindicator adenosine-5'-monophosphate, the adenosine portion of the molecule could be easily labelled with $H^3$ (tritium) and/or carbon$^{14}$ or the monophosphate portion could be labelled with phosphorus$^{32}$. The particular choice of labels and method of labelling depends upon the system being used. Tritium is more readily available and presents less of a biohazard. Phosphorus$^{32}$ has a shorter half-life and would be more sensitive because the adenosine-5'-monophosphate with phosphorus$^{32}$ would be more sensitive for scintillation counting. The radiolabelled indicators are commercially available and can be purified prior to use by conventionally known techniques. These compounds have the advantage over the radioactive products used in RIA in that they have a much longer shelf life and they are less subject to radiodegradation. Additionally, they are less expensive. The particular labelling of the other above-noted enzyme-radioindicator systems would be readily apparent to a person having ordinary skill in the art given the disclosure of the present invention herein.

The separating step of the present invention for separating the unreacted indicator from the radiolabelled products of the reaction between the radioindicator and the enzyme-conjugated antibody would also be readily apparent to a person having ordinary skill in the art considering the disclosure herein. Examples of possible methods include filtration, differential preciptiation, vaporation, chromatography, etc. One example and a currently preferred method of separation is by chromatography, and more specifically, liquid chromatography. The liquid chromatography preferably comprises passing the radiolabelled and unlabelled products through a selectively adsorbing ion exchange column. The ion exchange column can be packed with a cross-linked polymerized dextran ion exchange material such as Sephadex DEAE A-25. The ion exchange material can be positively or negatively charged. When using the preferred radioindicator, adenosine-5'-monophosphate, the unreacted adenosine-5'-monophosphate and phosphate which have negative charges are retained on the positively charged column while the adenosine which results from the reaction flows freely through the resin. If the adenosine is labelled with tritium and/or carbon[14], it can be placed directly into scintillation vials for scintillation counting. By alternating the ionic strength of the eluate, the phosphate can be placed in scintillation vials for scintillation counting. Other separation chromatographies can be used such as thin-layer chromatography, high pressure chromatography, paper chromatography, and the like.

The optimal dilution of the reagents utilized in the present inventive method are determined by checker board titration as disclosed in, for example, an article by Voller, et al. in *The Bulletin of W.H.O.* 53, pages 55–58, (1976).

The present invention yields the surprising result that it is a thousand-fold more sensitive than RIA or ELISA in detection of specific antigens. The present invention has been shown to be capable of measuring antigen concentrations as low as $10^{-17}$ grams per milliliter of antigen. As noted in one of the specific examples which follows, the lowest level of detection of cholera toxin for ELISA for a 1000 minute incubation period was $10^{-18}$ moles or $10^{-13}$ grams per milliliter while for the present invention the lowest level was $10^{-17}$ grams per milliliter or $10^{-22}$ moles. A similar result in terms of sensitivity was found for the present invention versus ELISA and RIA in a comparison of assays for human rotavirus, an important cause of infantile gastroenteritis.

Two of the major causes of diarrheal disease in humans are rotavirus and the enterotoxigenic strains of *Escherichia coli*. The heat-labile toxin produced by *E. coli* cross-reacts extensively with cholera toxin. Since infants and children are particularly susceptible to complications such as dehydration that are secondary to the acute enteritis caused by these agents, methods of rapid diagnosis are clinically important. ELISA and RIA have been recently used for this purpose. The present invention is an improved method of rapid diagnosis that is several orders of magnitude more sensitive than ELISA or RIA. Additionally, the present invention would also aid in the diagnosis of other viral agents such as herpes viruses, hepatitus virus, etc.

The present invention has distinct advantages over RIA and ELISA. The thousand-fold increase in sensitivity would be of particular importance not only in earlier diagnosis of the above-noted diseases but also in assays of antigens such as carcinogen-DNA adducts and hormone releasing factors that may be present in picogram and fematogram amounts. In these two noted cases, ELISA and RIA do not yield any results whereas the present invention has the necessary sensitivity. In the case of infectious agents and toxins, the increased sensitivity would be useful in the detection of the low concentrations of these agents that may be found in environmental samples. This would allow epidemiological surveys and studies to be made which were impossible in the past. The radioactive biohazards of the present invention with tritium and/or carbon[14] labelled radioindicators are less than those with RIA which generally uses radioactive iodine. While the cost of and equipment required for the present invention is greater than that required for ELISA, it is less expensive than RIA. The present invention could be used in both clinical and research laboratories to measure antigens, e.g., viruses, bacteria, parasites, toxins, drugs, tumor markers, hormones, etc., in solutions and mixtures such as blood, serum, feces, sputum, urine and environmental specimens.

BRIEF DESCRIPTION OF THE DRAWINGS

The advantages and features of the present invention will be more fully understood from the following description of general and detailed examples, taken in conjunction with the accompanying drawings, wherein:

FIG. 4a is a graph showing the percent of adenosine-5'-monophosphate converted by alkaline phosphatase IgG conjugate to adenosine;

FIG. 4b is a graph of the double reciprocal plot of Michalis-Menten equation of the alkaline phosphatase assay in FIG. 4a;

DETAILED DESCRIPTION OF GENERAL AND SPECIFIC EXAMPLES

Figure 1:
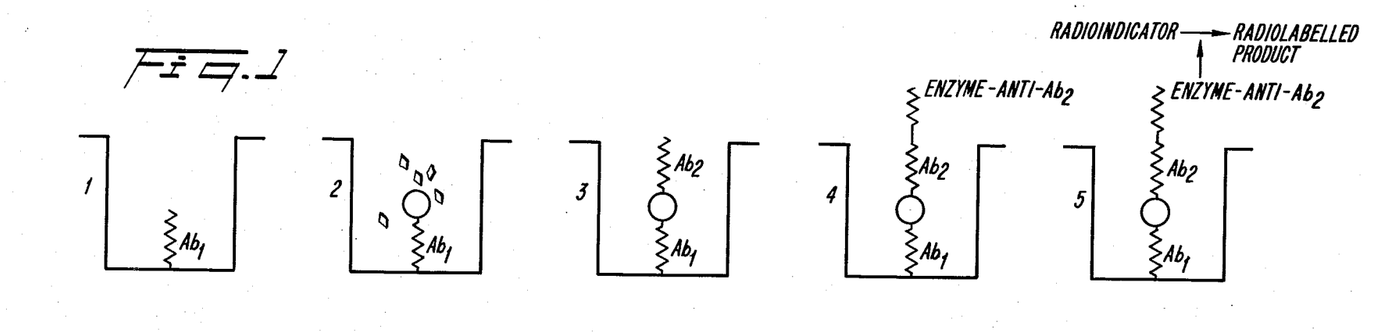
FIG. 1 is a diagrammatic illustration of the basic method steps for the indirect assay method for antigen measurement according to the present invention.

FIG. 1 shows in five steps a general example of the indirect assay method steps of the present invention in a test for a specific antigen. In Step 1, an antigen-reactive antibody (Ab$_1$) is adhered to a solid substrate such as the well of a microtiter plate. Any unadhered antibody is washed away. In Step 2, the test material is added. This can comprise specimen from a test patient or test animal, a soluted environmental sample or the like. Antigen, shown as a circle will adhere to the antibody pre-coat. Antigen negative material shown as small diamonds will be washed away in the following wash. The unreacted sample test material is washed away. In Step 3, unconjugated antigen-reactive antibody (Ab₂) from a different animal than Ab₁ is added. This reacts with the antigen that is adhered to Ab₁. The unreacted unconjugated antigen-reactive antibody Ab₂ is washed away. In Step 4, enzyme labelled antibody directed against one of the immunoglobulin subclasses of the animal source of Ab₂ is added. Preferably this is of the IgG globulin subclass because it is the most specific of the immunoglobulins. However, IgM, IgA, IgD or IgE could be used instead. This is the indirect linkage between the enzyme conjugated antibody and the antigen. The unreacted enzyme conjugated antibody is washed away. In Step 5, a radioindicator is added. The enzyme adhered to the well will convert the indicator to radioactive product(s), which are later separated from the unreacted indicator by chromatography. The separated radiolabelled product(s) are placed in a scintillation vial with a liquid scintillator and counted. The amount of radioactive product(s) is proportional to the amount of antigen in the initial test material.

Figure 2:
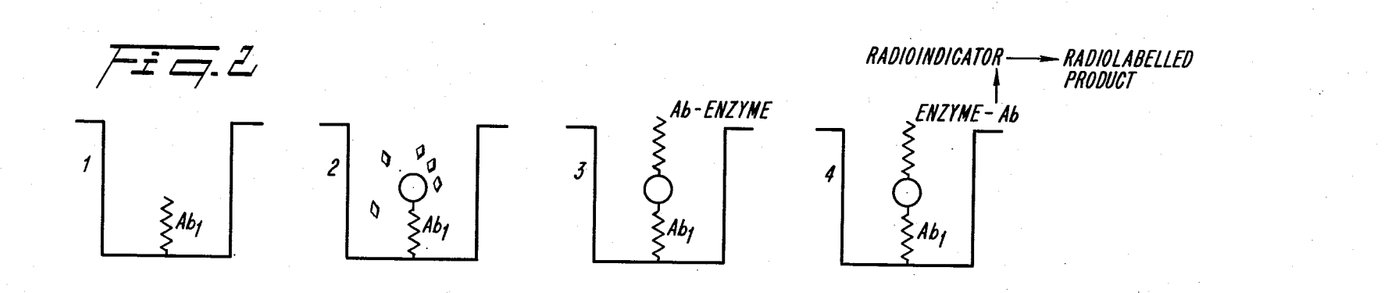
FIG. 2 is a diagrammatic illustration of the method steps for direct assay for antigen measurement according to the present invention.

FIG. 2 illustrates the method steps for the direct assay for antigen measurement in accordance with the present invention. In Step 1, an antigen-reactive antibody (Ab₁) is adhered to the solid substrate such as the well of a microtiter plate. The unadhered antibody is washed away. In Step 2, the test material such as specimen from a patient or animal or a soluted environmental sample is added. If it is antigen positive (antigen being shown by a circle) the antigen will adhere to the antibody precoat. Antigen negative material shown by small diamonds will be washed away. The antigen negative material is washed away. In Step 3, a second antigen-reactive antibody (Ab) conjugated with a particular enzyme is added. This antibody can be derived from the same host animal source as Ab₁ and is specific to the antigen. This will react with antigen that is adhered to Ab₁. This method is generally more expensive than the indirect method because the enzyme conjugated antibody is generally only available in small quantities because it is specific to a particular antigen. Losses result in the conjugating reaction which make the reagents very expensive. As noted previously, in the indirect method, enzyme-conjugated anti-Ab₂ is more readily available. The unreacted enzyme-conjugated antibody is washed away. In Step 4, a radioindicator is added. The enzyme adhered to the well will convert the indicator to radioactive product(s). These are subsequently separated from the unreacted indicator. The radioactive products are placed in a scintillation vial with a liquid scintillator and counted. The amount of radioactive products indicated by the counting is proportional to the amount of antigen in the initial test material.

Figure 3:
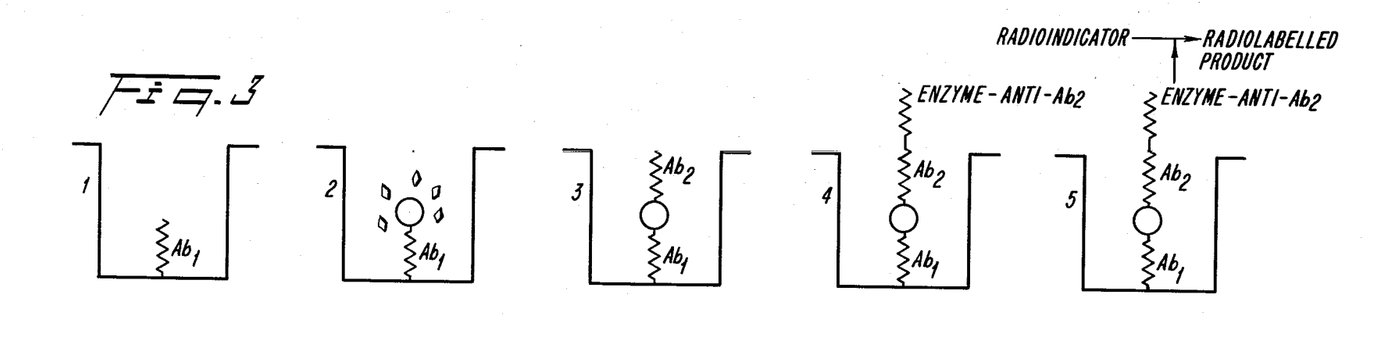
FIG. 3 is a diagrammatic illustration of the method steps for antibody measurement (binding assay) according to the present invention.

In FIG. 3, a method for testing for antibodies is shown in accordance with the present invention (a binding assay). In Step 1, an antibody (Ab₁) to an antigen is adhered to the solid substrate shown as a microtiter well. The excess antibody is washed away. In Step 2, the known antigen is added (shown as a circle). It will couple with the antigen-reactive antibody already adhered to the substrate. Any non-antigenic material shown as diamonds will be removed in the following washing. The non-antigenic material is washed away. In Step 3, the serum ro fluid to be tested is added. If it contains the antigen-reactive antibody (Ab₂) that is being tested for, this antibody Ab₂ will adhere to the antigen. The excess fluid is washed away. In Step 4, enzyme conjugated antibody directed against the immunoglobulin subclass (IgG, IgM, IgA, IgD, IgE) of the animal host source of Ab₂ is added. This enzyme conjugated antibody thus couples to the combination of Ab₂, antigen and Ab₁. Ab₂ acts as an antigen to this enzyme coupled antibody. The excess fluid is washed away. In Step 5, a radioindicator is added. The enzyme adhered through the coupling with Ab₂ will convert the radioindicator to radiolabelled product(s). These are separated from unreacted indicator. The radio-labelled product(s) are placed in a scintillation vial with a liquid scintillator and counted. The amount of radiolabelled product(s) as indicated by the counting is proportional to the amount of antibody being tested for in the original test material.

EXAMPLE I

PURIFICATION OF TRITIUM-LABELLED ADENOSINE-5'-MONOPHOSPHATE

Adenosine-5'-monophosphate labelled with tritium $H^3$ was commercially obtained. The radioactivity of this material was approximately 15 Ci per millimole. It was purified by column chromatography with an ion exchange material, DEAE Sephadex, a cross-linked polysaccharide dextran. The purification was carried out in a stepwise manner. Two millicurie of the tritium-labelled adenosine-5'-monophosphate in 0.2 ml of distilled water was applied to a disposable column containing 2 ml of DEAE Sephadex. The contaminating tritium-labelled adenosine was eluted with distilled water and discarded. The tritium-labelled adenosine-5'-monophosphate was eluted with 0.2 molar ammonium carbonate and after lypholization to remove the ammonium carbonate, the tritium-labelled adenosine-5'-monophosphate was dissolved in 50% ethanol. The thus purified tritium-labelled adenosine-5'-monophosphate contained less than 0.2% tritium-adenosine and was stable at $-20°$ C. for at least three months.

EXAMPLE II

DETERMINATION OF OPTIMAL ASSAY CONDITIONS

Figure 4:
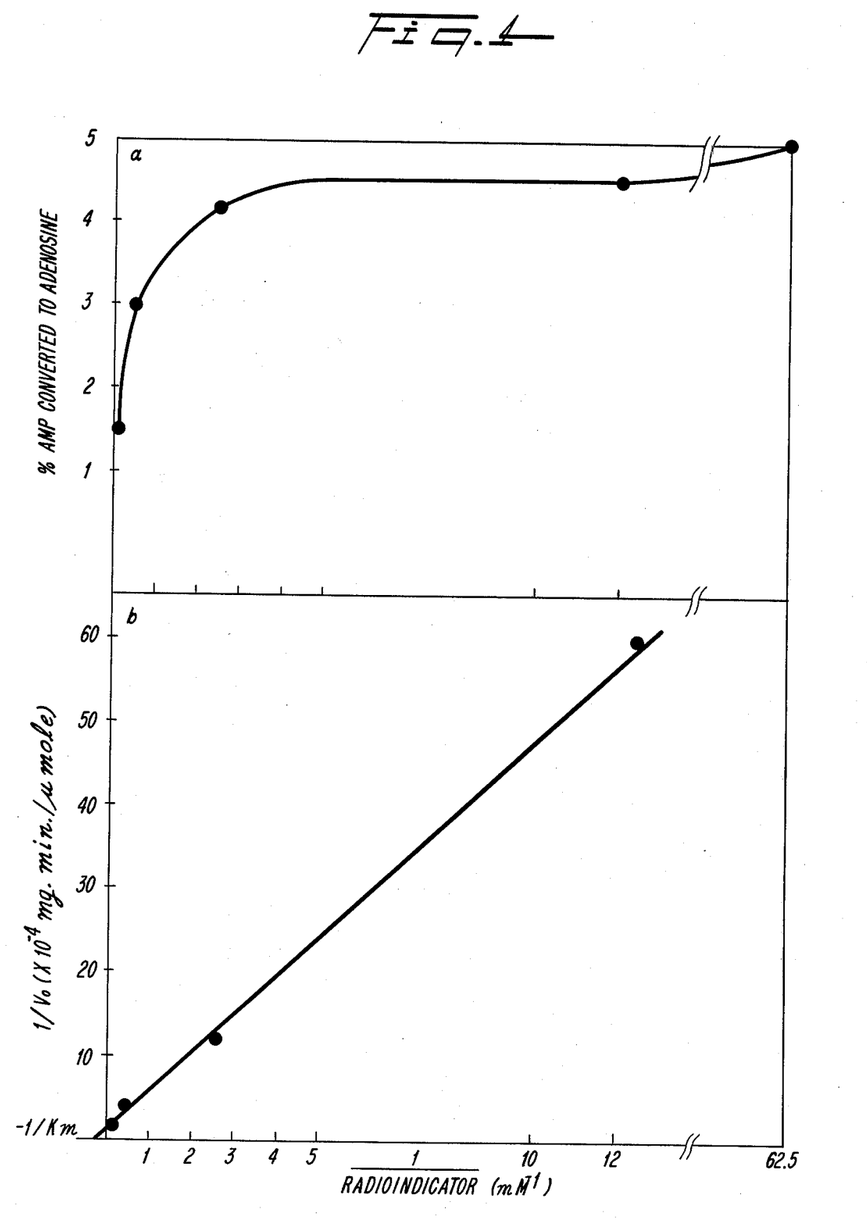
Figure 5:
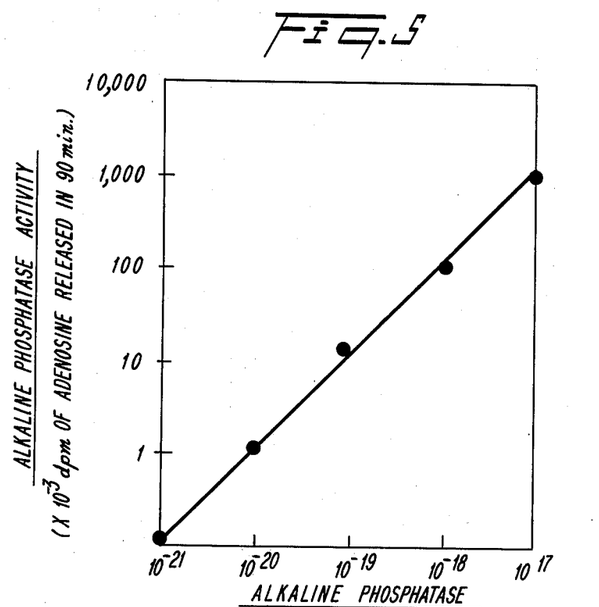
FIG. 5 is a graph illustrating the determination of the sensitivity of the assay according to the present invention.

To determine the enzyme kinetics of alkaline phosphatase-IgG (goat anti-rabbit) conjugate, varying concentrations of adenosine-5'-monophosphate were added to a $10^6$ dilution of the enzyme-IgG conjugate. FIG. 4a shows the percent of adenosine-5'-monophosphate (AMP) converted by alkaline phosphatase IgG conjugate to adenosine. Alkaline phosphatase conjugate ($2 \times 10^{-8}$ milligrams per milliliter) was added to 10 mM diethanolamine buffer having a pH of 9.8, containing various concentrations of AMP. The reaction mixtures were incubated at 37° C. for 30 minutes. The tritium-labelled adenosine released was determined by column chromatography utilizing DEAE Sephadex by applying an 0.05 milliliter aliquot of the reaction mixture to a column packed with 1.5 milliliters DEAE Sephadex A-25 followed by elutation with a total of 4.5 milliliters of 0.01 M diethanolamine buffer with a pH of 9.8, containing 0.1 mM unlabelled adenosine in two fractions. 20 ml of liquid scintillator, Aquasol ®, was added to each fraction and the tritium-labelled adenosine was measured in a liquid scintillation counter. The Km was calculated to be approximately 4 mM by a double reciprocal plot of the Michalis-Menton equation which is shown in FIG. 4b. When the fraction of tritium-labelled AMP converted to tritium-labelled adenosine was plotted against the concentration of tritium-AMP (FIG. 4a), a higher percentage of tritium-AMP converted to tritium-adenosine was seen at the lowest radioindicator concentration. Based on these results, the tritium-AMP concentration of approximately 1 micromole ($3 \times 10^6$ DPM) was used in subsequent experiments. The counting of the actual scintillation counter was adjusted in accordance with standard techniques to yield DPM, disintegrations per minute. Varying concentrations of diethanolomine buffer and $MgCl_2$ were tested. The addition of $MgCl_2$ to the mixture enhanced the non-enzymatic hydrolysis of tritium-AMP. The enzyme activity of alkaline phosphatase decreased with diethanolamine concentrations of 1 mM or less.

EXAMPLE III

DETERMINATION OF SENSITIVITY OF THE ASSAY

Various dilutions of alkaline phosphatase ($10^{-17}$ to $10^{-21}$ mole) were included in 0.1 ml reaction volumes of 10 mM diethanolamine buffer at pH 9 containing 100 picamole tritium-AMP as a radioindicator. The products were isolated as above by DEAE Sephadex column chromatography. The activity is expressed as adenosine (DPM) released in 90 minutes. As shown in FIG. 2, the method can detect enzyme levels of $10^{-12}$ milligrams per milliliter, i.e., $10^{-20}$ moles alkaline phosphatase. The release of tritium-adenosine was linear for enzyme concentrations of $10^{-17}$ to $10^{-20}$ mole in an incubation volume of 0.1 ml during the 90 minute assay. At these enzyme concentrations, similar results were obtained when the pH of the reaction mixture was either 9.0 or 9.8.

EXAMPLE IV

TIME COURSE STUDY OF ALKALINE PHOSPHATASE-IgG CONJUGATE REACTION

Figure 6:
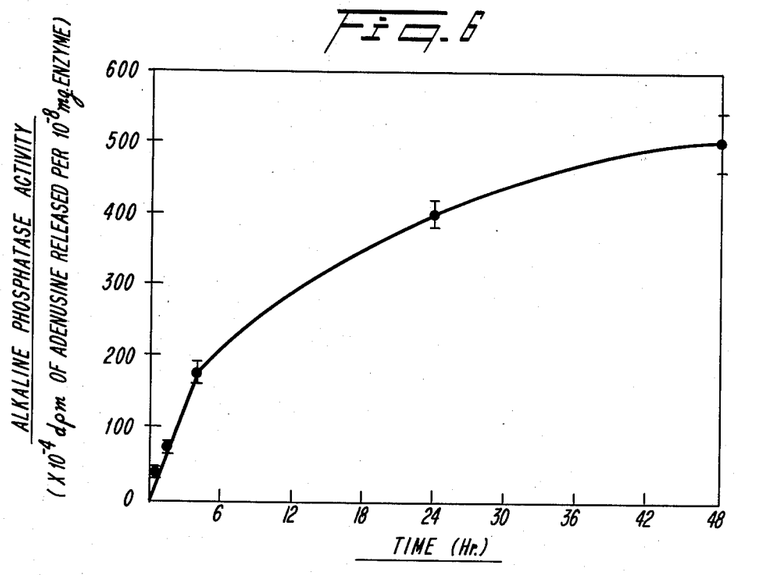
FIG. 6 is a graph of the time course of alkaline phosphatase-IgG conjugate reaction according to the present invention.

Triplicates of the assay mixture containing 100 picamole of tritium-AMP and $10^{-8}$ milligrams of enzyme conjugate in 0.1 milliliter of 10 mM buffer with a pH of 9.0 were incubated at 37° C. from 0 to 48 hours. Aliquots of 50 microliters of the reaction mixtures were withdrawn for determination of enzyme activity at 0.5, 1.5, 4.5, 24 and 48 hours. The results of these samples is shown in FIG. 6. The enzyme activity was nearly linear for 90 minutes with approximately 2% of the tritium-AMP hydrolyzed to tritium-adenosine and phosphate. At 24 and 48 hours, the enzyme reaction became slower. Since the tritium-AMP radioindicator was still in excess, the reduction of enzyme activity could be secondary to enzyme degradation and/or product inhibition. To determine the effects of reaction products on the assay, either phosphate (2 or 20 picamoles) or adenosine (20 picamoles) was added to the assay mixtures. 2 and 20 picamole phosphate inhibited alkaline phosphatase activity by 8% and 90% respectively. 20 picamole adenosine caused no detectable effect in the activity of the adenosine phosphatase. The variation in the triplicate samples was small. For reaction times of less than 5 hours, the variation in either duplicate or triplicate samples was less than 10% of the mean value.

EXAMPLE V

PREPARATION OF ALKALINE PHOSPHATASE-CONJUGATED ANTI-SERA

As one example of commonly used conjugation methods, the following procedure is used to prepare goat-anti-guinea pig sera. Phosphate-buffered saline (PBS; pH 7.4) in the amount of 1.0 milliliters is added to 1.0 milliliters of anti-serum. To this mixture, 2.0 milliliters of 36% $Na_2SO_4$ is added. This mixture is stirred gently for 30 minutes at room temperature. The mixture is centrifuged at 3000 xg for 10 minutes. The supernatant is discarded. The precipitate is washed twice in 18% $Na_2SO_4$ solution. The precipitate after washing is centrifuged again and the supernatant is discarded. The precipitate is dissolved in 0.8 ml of PBS. An equal quantity of 24% $Na_2SO_4$ solution is added. This is centrifuged at 3000 xg for 10 minutes. The resulting precipitate is washed with 12% $Na_2SO_4$. The precipitate is redissolved in 1.0 ml of PBS and is transferred to a dialysis sack. It is dialyzed for 3 days at $+4°$ C. against PBS. To remove insoluble material, the solution after dialysis can be centrifuged at 5000 rpm for 10 minutes. The precipitate is discarded and the supernatant is labelled for further use. Protein concentration can be determined by optical density adsorption at 280 nm. Thus, the anti-serum is ready for conjugation.

The alkaline phosphatase is commercially available. It can be available from calf mucosa, Sigma type VII, with a specific activity of 300–1100 units per mg. The enzyme suspension is centrifuged and the supernatant discarded. 2 milligrams of the above prepared anti-serum in 1 milliliter of PBS is added to 5 milligrams of enzyme. This is mixed at room temperature. The mixture is dialyzed extensively at $+4°$ C. with several changes of PBS. The dialyzed solution has 25% glutaraldehyde added to it to give a final concentration of 0.2%. This is incubated for 1 to 2 hours at room temperature and then dialyzed again at $+4°$ C. against three changes of PBS. The dialysis tube is transferred to a 0.05 molar tris-(hydroxymethyl)aminomethane buffer with a pH of 8.0. The dialysis is continued extensively at $+4°$ C. with three changes of buffer. The thus produced conjugate is diluted to 4.0 ml with tris buffer containing 1.0% fetal calf serum and 0.02% sodium azide. This is stored in the dark at $+4°$ C. In the above manner, the enzyme-conjugated antibody is prepared.

EXAMPLE VI

MEASURING CHOLERA TOXIN

In accordance with the present invention, cholera toxin was measured as follows:

Polyvinyl round bottomed microtiter plates were coated with a 0.1 ml aliquot of burro anti-cholera toxin diluted at 1:10,000 in 0.06 M carbonate buffer at a pH of 9.8, for 14 hours at 4° C. This procedure adhered the burro anti-cholera antibody to the solid substrate. The wells of the plates were washed five times in phosphate buffered saline (PBS; pH 7.4) containing 0.5 ml of a detergent, Tween 20, per liter (PBS-Tween). An 0.1 ml aliquot of either cholera toxin dilution or solvent (for a negative control) was added in duplicate to the wells. The negative controls consisted of five filtrates from strains of *E. coli* which do not produce any detectable toxin. The plates were incubated for 14 hours at 4° C. Thus, an antigen was coupled to the solid substrate.

After another washing procedure, as above with PBS-Tween, a 0.1 ml aliquot of guinea pig anti-cholera toxin diluted 1:400 in PBS-Tween containing 1% normal horse serum was added. The normal horse serum is added to the diluent both to saturate any unbound sites in the well and to minimize the cross-reactivity with the burro serum bond to the well. The plates were incubated for one hour at 37° C. Thus, an unconjugated antibody from a different animal source from the adhered antibody was reacted with the coupled antigen.

After another washing procedure as above with PBS-Tween, 0.1 milliliter aliquots of alkaline phosphatase conjugated goat anti-guinea pig IgG, (diluted 1:800, as prepared in Example V) was added to each well. The enzyme-conjugated antibody reacts with the adhered unconjugated antibody and antigen.

After another washing procedure, 0.1 ml aliquots of tritium-adenosine-5'-monophosphate (tritium-AMP) ($3 \times 10^6$ CPM; $1.0 \times 10^{-10}$ moles) diluted in 0.01 mM diethanolamine, pH 9.0, were added to each well.

After 10, 100, or 1,000 minutes, the tritium-adenosine produced by the reaction of the alkaline phosphotase IgG conjugate bound to the antigen with the tritium-AMP radioindicator is separated by applying an 0.05 ml aliquot of the reaction mixture to a column packed with 1.5 ml ion exchange resin, DEAE Sephadex A-25 (cross-linked polysaccharide dextran). This was followed by elutation with a total of 4.5 ml of 0.1 M diethanolamine buffer pH 9.8, containing 0.1 mM adenosine in two fractions. 20 ml of a liquid scintillator, Aquasol®, was added to each fraction and the tritium-adenosine was measured in a liquid scintillation counter. As an alkaline phosphatase negative control, 0.1 ml aliquots of tritium-AMP were incubated at 37° C. without the enzyme conjugate for the same length of time as the test specimens. 0.05 ml of the negative control was passed through the DEAE ion exchange column to determine the amount of tritium-adenosine formed in the absence of the enzyme. The enzyme-specific activity was determined by subtracting this value from that obtained from the test specimen. In addition, five filtrates from non-cholera toxin producing organisms (*E. coli*) were run in each test. A test well was considered positive for cholera toxin if it yielded an enzyme specific activity that was two standard deviations greater than the mean toxin-free control value. The assays were run in duplicate and the variation between duplicates was less than 5%. The results are shown in Table 1.

EXAMPLE VII

ELISA MEASURING OF CHOLERA TOXIN

The measurement tests for cholera toxin utilizing ELISA were performed identically with Example VI with the exception that tritium-AMP was not used as an indicator for the alkaline phosphatase. Instead, p-nitrophenylphosphate was used diluted 1 milligram per milliliter in 0.1 mM diethanolamine buffer, pH 9.8, containing 0.01 mM $MgCl_2$. The rate of enzymatic reaction was determined by measuring the formation of yellow-colored products at 405 nm in a spectrophotometer. This was accomplished in general accordance with the methods outlined in Yolken, et al., *Journal of Clinical Microbiology*, Volume No. 6, No. 5, November, 1977, pages 439–444 and Engvall, et al., *Journal of Immunology*, Volume No. 109, 1972, pages 129–135. The results of this test are presented in comparison with the method according to the present invention in Table 1.

The comparison of ELISA and the present invention for the detection of cholera toxin is shown in Table 1. Using a reaction time of 1000 minutes, ELISA can detect $10^{-13}$ grams, i.e., approximately $6 \times 10^5$ molecules of cholera toxin. The present invention can surprisingly detect ten-fold lower amounts of toxin with a shorter incubation time of 10 minutes. At a comparable incubation time of 1000 minutes, $10^{-16}$ grams, i.e., $6 \times 10^2$ molecules of toxin can be detected with the present invention. This thousand-fold increase in sensitivity is extremely unexpected.

It would be readily apparent to a person having skill in the art that the present inventive method could be used in blocking assays as are well-known in the art.

TABLE 1

| COMPARISON OF ASSAYS FOR CHOLERA TOXIN[1] | | | | | |
|---|---|---|---|---|---|
| Cholera Toxin | | ELISA[2] | USERIA[3] | | |
| (g) | (M) | (1,000 min) | 10 min | 100 min | 1,000 min |
| $10^{-10}$ | $10^{-15}$ | 1.61 ± 0.14 | 759 ± 8 | 3882 ± 36 | 8799 ± 63 |
| $10^{-11}$ | $10^{-16}$ | 0.77 ± 0.09 | 189 ± 12 | 483 ± 18 | 2205 ± 66 |
| $10^{-12}$ | $10^{-17}$ | 0.26 ± 0.05 | 24 ± 6 | 186 ± 12 | 696 ± 36 |
| $10^{-13}$ | $10^{-18}$ | 0.08 ± 0.03 | 18 ± 6 | 126 ± 9 | 567 ± 33 |
| $10^{-14}$ | $10^{-19}$ | 0.0 | 15 ± 6 | 93 ± 9 | 408 ± 27 |
| $10^{-15}$ | $10^{-20}$ | 0.0 | 6 ± 6 | 57 ± 6 | 291 ± 24 |
| $10^{-16}$ | $10^{-21}$ | 0.0 | 0 | 9 ± 6 | 93 ± 21 |
| $10^{-17}$ | $10^{-22}$ | 0.0 | 0 | 0 | 3 ± 15 |

Note
[1]Values (means ± S.D.) underlined have a significance value of $p < 0.025$ (Students t test) when compared to control.

Note
[2]Enzyme-linked immunosorbent assay (ELISA); values are expressed as units of optical density at 405 nanometers.

Note
[3]Ultrasensitive enzymatic radioimmune assay, i.e. the present invention, (USERIA); values are expressed as dpm ($\times 10^{-2}$) of $^3$H-adenosine produced during 10, 100, and 1,000 minutes of incubation time.

EXAMPLE VIII

MEASUREMENT OF ROTAVIRUS

Rotavirus, a 70 nm virus which is also called human reovirus-like agent (HRVLA), duovirus and infantile gastroenteritis virus, is an important cause of gastroenteritis in infants and young children in several parts of the world. Diagnosis of rotavirus gastroenteritis has been hampered because the agent does not grow well in tissue-culture. Direct display of negatively stained virus particles by electronmicroscopy (E.M.) has proved to be a reliable means of diagnosis as well as radioimmunassay (RIA) and ELISA. The present invention also provides a specific test for rotavirus.

The measurement of rotavirus was performed in a similar manner to that of Example VI described above with the exception that goat anti-rotavirus serum was substituted for burro anti-cholera toxin, guinea pig anti-rotavirus serum was substituted for guinea pig anti-cholera toxin and normal goat serum was substituted for normal horse serum in the dilution step. The stool specimens were prepared utilizing a standard known technique as for example taught by Yolken, et al., in *The Lancet*, Aug. 6, 1977, pages 263–268 and Yolken, et al., *Science*, Volume 201, July 21, 1978, pages 259–262. Five stool specimens from normal children were added to each assay as negative controls. A dilution of a standard filtrate was considered positive for rotavirus if it had a value of two standard deviations greater than the mean of the five controls. The results of these assays are presented in Table 2.

EXAMPLE IX

MEASUREMENT FOR ROTAVIRUS UTILIZING ELISA

The same specimens as tested in Example VIII were tested utilizing ELISA as taught by Yolken, et al. in *The Lancet*, Aug. 6, 1977, pages 263–268. Basically, instead of tritium-AMP, as a radioindicator for alkaline phosphatase, ELISA used p-nitrophenylphosphate diluted 1 milligram per milliliter in 0.1 mM diethanolamine buffer, pH 9.8, containing 0.01 mM $MgCl_2$. The rate of enzymatic reaction was determined by measuring the formation of yellow-colored product at 405 nm in a spectrophotometer. The results are presented in Table 2.

EXAMPLE X

MEASUREMENT FOR ROTAVIRUS UTILIZING RIA

The same specimens which were assayed in Examples VIII and IX were also assayed utilizing radioimmunoassay (RIA) techniques similar to those disclosed by Greenberg, et al. in *Infection and Immunity*, Volume No. 17, No. 3, September, 1977, pages 541–545. Basically, purified guinea pig anti-rotavirus IgG was labelled with iodine[125] (about 20 microcurie/micrograms of protein). The labelled immunoglobulin was diluted 1:1 in fetal calf serum and stored at 4° C. A solid-phase microtiter test was used. Polyvinyl microtiter plates were precoated with goat anti-rotavirus serum diluted in PBS. The optimal dilution of anti-serum was determined by checker board titration. After incubation, the wells are washed with PBS. 50 microliters of the test specimens were added to the wells and allowed to incubate at room temperature. The wells were then washed with PBS and 50 microliters of iodine[125]-labelled guinea pig anti-rotavirus serum was added to each well. Following incubation, the plates were again washed and cut up with a scissors. The separate wells were placed in gamma-counting tubes for analysis. Results were expressed as a ratio of residual counts in the sample well to the mean of residual counts in wells run as controls. A positive/negative (P/N) ratio of 1.7 or greater is considered to be positive for rotavirus. The results are shown in Table 2.

In Table 2, the present invention is compared with both RIA and ELISA for the detection of rotavirus. As can be readily seen, the present invention is one hundred-fold more sensitive than ELISA and one thousand-fold more sensitive than RIA.

experimental purposes. The surprising increase in sensitivity is shown.

The embodiments of the invention in which an exclusive property or privilege is claimed are defined as follows:

1. A method of quantitatively measuring the concentration of an immunosystem reactant comprising:
    (a) preparing a solid substrate;
    (b) selectively adhering the immunosystem reactant to said substrate;
    (c) binding an enzyme-conjugated antibody to said reactant;
    (d) reacting a radiolabelled indicator with said enzyme-conjugated antibody thereby producing a radiolabelled product and an unlabelled product;
    (e) separating said radiolabelled product(s) from unreacted indicator; and
    (f) measuring the extent of reaction by radioactive counting said radiolabelled product, said counting yielding a quantitative measurement of the concentration.

2. The method according to claim 1 wherein the immunosystem reactant being measured is a specific antigen.

3. The method according to claim 1 wherein the immunosystem reactant being measured is a single specific antigen-reactive antibody of a particular animal source; step (a) comprises adhering an antigen to said substrate, said antigen being specific to said antibody being measured; step (b) comprises reacting said antibody with said adhered antigen, thereby bending said antibody to said adhered antigen; and step (c) comprises reacting said enzyme-conjugated antibody with said adhered antibody, said enzyme conjugated antibody being selected from the group directed against the immunoglobulin subclass of the animal source of said adhered antibody, thereby binding said enzyme-conjugated antibody to said adhered antibody.

4. The method according to claim 2 wherein step (a)

TABLE 2

| | COMPARISON OF ASSAYS FOR ROTAVIRUS[1] | | | | |
|---|---|---|---|---|---|
| Dilution of | ELISA[3] | RIA[4] | USERIA[5] | | |
| Standard[2] | (1,000 min) | (P/N) | (10 min) | (100 min) | (1,000 min) |
| $10^{-2}$ | 0.94 ± 0.10 | 10.7 | 3507 ± 333 | 11871 ± 558 | 19362 ± 687 |
| $10^{-3}$ | 0.45 ± 0.04 | 5.3 | 732 ± 54 | 2697 ± 126 | 8646 ± 399 |
| $10^{-4}$ | 0.11 ± 0.02 | 1.2 | 123 ± 12 | 483 ± 24 | 3036 ± 144 |
| $10^{-5}$ | 0.0 | 1.0 | 12 ± 3 | 93 ± 12 | 1092 ± 57 |
| $10^{-6}$ | 0.0 | 1.0 | 0.0 | 21 ± 9 | 528 ± 33 |
| $10^{-7}$ | 0.0 | 1.0 | 0.0 | 0.0 | 27 ± 18 |

Note
[1]Values (mean ± S.D.) underlined have a significant value of p <0.025 (Students t test) when compared to control.
Note
[2]$10^3$ of virus particles per 5 squares (400 mesh electron microscope grids).
Note
[3]Enzyme-linked immunosorbent assay (ELISA); values are expressed as units of optical density at 405 nanometers.
Note
[4]Radioimmune assay (RIA); values are expressed as ratio of positive (P) to negative (N) values.
Note
[5]Ultrasensitive enzymatic radioimmune assay i.e., the present invention, (USERIA); values are expressed as dpm ($\times 10^{-2}$) $^3$H-adenosine produced during 10, 100 and 1,000 min of incubation time.

Thus, it is readily apparent that the present invention is suitable for quantitatively and qualitatively measuring immunosystem reactants such as antibodies or antigens, for example, viruses, bacteria, parasites, hormones, toxins, tumor markers, drugs, etc., in complex mixtures and solutions such as body fluids and environmental specimens for diagnostic, prognostic, epidemiological and comprises adhering an antigen-reactive antibody to said substrate, said antigen reactive antibody being specific for said antigen and step (b) comprises reacting said antigen with said adhered antibody.

5. The method according to claim 2 wherein said enzyme-conjugated antibody is specific for said antigen and step (c) comprises reacting said enzyme-conjugated antibody directly with said adhered antigen.

6. The method according to claim 2 wherein step (c) comprises reacting an unconjugated antigen-specific antibody to said adhered antigen, said unconjugated antibody being from a different animal source than said adhered antibody; and reacting said enzyme-conjugated antibody with said unconjugated antibody, said enzyme-conjugated antibody being selected from the group directed against the immunoglobulin subclass of the animal source of said unconjugated antibody, thereby binding said enzyme-conjugated antibody to said antigen.

7. The method according to claim 6 wherein step (a) comprises adhering an antigen-reactive antibody to said substrate, said antigen reactive antibody being specific for said antigen and step (b) comprises reacting said antigen with said adhered antibody.

8. The method according to any one of claims 1, 2, 3, 4, 5, 6, or 7, wherein said radiolabelled indicator is radioactively labelled adenosine-5'-monophosphate.

9. The method according to claim 8 wherein said adenosine-5'-monophosphate is labelled with $H^3$ and/or carbon$^{14}$.

10. The method according to claim 8 wherein said adenosine-5'-monophosphate is labelled with $P^{32}$.

11. The method according to any one of claims 1, 2, 3, 4, 5, 6 or 7, wherein said enzyme-conjugated antibody is an antibody conjugated with alkaline phosphatase.

12. The method according to claim 11 wherein said antibody is IgG globulin.

13. The method according to claim 1 wherein step (e) comprises chromatography.

14. The method according to claim 13 wherein said chromatography comprises liquid chromatography.

15. The method according to claim 14 wherein said liquid chromatography comprises passing said radiolabelled and said unlabelled products through a selectively adsorbing ion exchange column.

16. The method according to claim 15, wherein said ion exchange column is packed with cross-linked polymerized dextran ion exchange material.

17. The method according to claim 14 wherein said chromatography comprises thin-layer chromatography.

18. The method according to claim 14 wherein said chromatography comprises high pressure chromatography.

19. The method according to either claim 6 or 7, wherein the antigen is cholera toxin.

20. The method according to either claim 6 or 7, wherein the antigen is human rotavirus.

* * * * *